United States Patent
Okuno et al.

(10) Patent No.: US 8,779,173 B2
(45) Date of Patent: Jul. 15, 2014

(54) METHOD OF PREPARING SILICA COMPOSITE PARTICLES

(71) Applicant: Fuji Xerox Co., Ltd., Tokyo (JP)

(72) Inventors: Hiroyoshi Okuno, Kanagawa (JP); Takeshi Iwanaga, Kanagawa (JP); Yoshifumi Iida, Kanagawa (JP); Chika Hama, Kanagawa (JP); Yasunobu Kashima, Kanagawa (JP); Shunsuke Nozaki, Kanagawa (JP)

(73) Assignee: Fuji Xerox Co., Ltd., Tokyo (JP)

( * ) Notice: Subject to any disclaimer, the term of this patent is extended or adjusted under 35 U.S.C. 154(b) by 7 days.

(21) Appl. No.: 13/749,304

(22) Filed: Jan. 24, 2013

(65) Prior Publication Data

US 2013/0331591 A1  Dec. 12, 2013

(30) Foreign Application Priority Data

Jun. 8, 2012 (JP) ................. 2012-130678

(51) Int. Cl.
*C07F 19/00* (2006.01)

(52) U.S. Cl.
USPC ............................................ 556/10; 556/173

(58) Field of Classification Search
USPC ..................................................... 556/10, 173
See application file for complete search history.

(56) References Cited

U.S. PATENT DOCUMENTS 5,763,085 A  6/1998 Atarashi et al.
6,048,574 A  4/2000 Atarashi et al.

FOREIGN PATENT DOCUMENTS

| JP | A-05-257150 | 10/1993 |
| JP | A-06-228604 | 8/1994 |
| JP | A-2007-022827 | 2/2007 |
| JP | A-2008-133386 | 6/2008 |

*Primary Examiner* — Porfirio Nazario Gonzalez
(74) *Attorney, Agent, or Firm* — Oliff PLC

(57) ABSTRACT

Provided is a method of preparing silica composite particles, including treating silica particles, wherein the treating is for treating the silica particles with a metal compound in which a metal atom binds to an organic group via an oxygen atom, in supercritical carbon dioxide, and the metal atom is selected from a group consisting of Ti, Al, Zr, V, and Mg.

16 Claims, No Drawings

METHOD OF PREPARING SILICA COMPOSITE PARTICLES

CROSS-REFERENCE TO RELATED APPLICATIONS

This application is based on and claims priority under 35 USC 119 from Japanese Patent Application No. 2012-130678 filed Jun. 8, 2012.

BACKGROUND

Technical Field

The present invention relates to a method of preparing silica composite particles.

SUMMARY

According to an aspect of the invention, there is provided a method of preparing silica composite particles, including treating silica particles, wherein the treating is for treating silica particles with a metal compound in which a metal atom binds to an organic group via an oxygen atom, in supercritical carbon dioxide, and the metal atom is selected from a group consisting of Ti, Al, Zr, V, and Mg.

DETAILED DESCRIPTION

Exemplary embodiments as an example of the present invention will be described in detail.

The method of preparing silica composite particles according to the present exemplary embodiment includes a step of treating the surface of silica particles with a metal compound in which a metal atom selected from a group consisting of Ti, Al, Zr, V, and Mg binds to an organic group via an oxygen atom, in supercritical carbon dioxide.

Herein, in the related art, for example, a method of preparing silica composite particles such as silica-titania, silica-alumina, and silica-zirconia by combining silicon alkoxide (alkoxide silane) and an alkoxide of a metal (hereinafter, called a "dissimilar metal") other than silicon is known.

As such a method of preparing silica composite particles, a method of treating the surface of silica particles by using an alkoxide of a dissimilar metal to form a layer treated with an oxide of a dissimilar metal is known.

The silica composite particles obtained by this method are preferable in the respect that the particles have functions that are not obtained from silica particles constituted only with silica. For example, the amount of moisture that silica particles absorb depends greatly on the environment due to the influence of silanol groups on the surface thereof. In addition, the electrical resistance or charge amount of the silica particles decreases under a high temperature and high humidity and increases under a low temperature and low humidity. Accordingly, if the particles are made into composite particles with a dissimilar metal, it is expected that environmental stability of the electrical resistance and chargeability will be improved.

However, for example, an alkoxide of a dissimilar metal such as titanium alkoxide or aluminum alkoxide more rapidly causes a hydrolysis reaction and a condensation reaction compared to silicon alkoxide, and the surface treatment using the alkoxide of a dissimilar metal is not evenly performed. Therefore, the environmental stability of the electrical resistance and chargeability has not been sufficiently improved in the current circumstances.

Moreover, though a technique not using the alkoxide of a dissimilar metal is also known, in this technique, a chemical bond between the silica particles and the layer treated with a metal oxide is weak, and the surface treatment is not evenly performed. Therefore, the environmental stability of the electrical resistance and chargeability has not been sufficiently improved by the technique in the current circumstances.

Accordingly, in the method of preparing silica composite particles according to the exemplary embodiment, the surface of silica particles is treated with a metal compound in supercritical carbon dioxide. By doing this, in the method of preparing silica composite particles according to the exemplary embodiment, silica composite particles having excellent environmental stability of the electrical resistance and chargeability are prepared.

Though unclear, the reason is considered to be as below.

It is considered that if the surface of silica particles is treated with a metal compound in supercritical carbon dioxide, a state where the metal compound is dissolved in the supercritical carbon dioxide is generated. The supercritical carbon dioxide has a characteristic of having an extremely low interfacial tension. Therefore, it is considered that the metal compound dissolved in the supercritical carbon dioxide easily diffuses to and reaches deep inside cavities of the surfaces of the silica particles together with the supercritical carbon dioxide. It is also considered that for this reason, the surface treatment is performed not only on the surface of the silica particles, but also on a portion deep inside the cavities.

Therefore, it is considered that if the surface of the silica particles is treated with a metal compound in supercritical carbon dioxide, the surface treatment may be performed more evenly.

For the above reason, it is considered that in the method of preparing silica composite particles according to the exemplary embodiment, silica composite particles having excellent environmental stability of the electrical resistance and chargeability are prepared.

It is also considered that in the method of preparing silica composite particles according to the present exemplary embodiment, generation of coarse powder is also inhibited. Compared to silicon alkoxide, the alkoxide of a dissimilar metal more rapidly causes hydrolysis and a condensation reaction. In addition, it is difficult to control the aggregation of the alkoxides of a dissimilar metal, and coarse powder is easily formed due to the aggregation of particles. However, it is considered that if the surface treatment is performed in supercritical carbon dioxide, the alkoxides of a dissimilar metal are inhibited from aggregating with each other, and consequently, formation of coarse powder is also inhibited.

Particularly, compared to fumed silica particles obtained by a gas-phase method or molten silica particles, sol-gel silica particles (silica particles obtained by a sol-gel method) have many silanol groups on the surface thereof or inside the cavities. Therefore, coarse powder is easily formed, and the environmental stability of the electrical resistance and chargeability tends to deteriorate. However, these problems may be improved by the method of preparing silica composite particles according to the exemplary embodiment even if the sol-gel silica particles are used as silica particles to be subjected to the surface treatment, and in this respect, the method is advantageous.

In addition, the silica particles to be subjected to the surface treatment are not limited to the sol-gel silica particles, and may be aqueous colloidal silica particles, alcoholic silica particles, fumed silica particles obtained by a gas-phase method, or molten silica particles.

The silica composite particles according to the exemplary embodiment are preferably subjected to a step of treating the surface of the silica particles of which the surface has been treated with a metal compound, by using a hydrophobizing agent (hydrophobizing treatment). By performing the hydrophobizing treatment using a hydrophobizing agent, the silica composite particles having excellent environmental stability of the electrical resistance and chargeability are more effectively prepared.

Herein, in the method of preparing silica composite particles according to the exemplary embodiment, supercritical carbon dioxide is used in the step of treating the surface of the silica particles by using a metal compound. However, the supercritical carbon dioxide may be used in other processes (for example, a solvent removing step or a hydrophobizing treatment step) of preparing the silica composite particles.

Examples of the method of preparing silica composite particles that uses supercritical carbon dioxide in other preparation processes include a method of preparing silica composite particles that includes a step of preparing a silica particle dispersion that contains silica particles and a solvent containing alcohol and water (hereinafter, called a "dispersion preparing step"), a step of removing the solvent from the silica particle dispersion by injecting supercritical carbon dioxide (hereinafter, called a "solvent removing step"), a step of treating the surface of the silica particles obtained after the solvent removal, in supercritical carbon dioxide by using a metal compound in which a metal atom selected from a group consisting of Ti, Al, Zr, V, and Mg binds to an organic group via an oxygen atom (hereinafter, called a "surface treatment step"), and a step of treating the surface of the silica particles of which the surface has been treated with the metal compound, in supercritical carbon dioxide with a hydrophobizing agent (hereinafter, called a "hydrophobizing treatment step").

In the method of preparing silica composite particles that uses supercritical carbon dioxide in other preparation processes, silica composite particles having excellent environmental stability of the electrical resistance and chargeability are prepared more effectively, and formation of coarse powder is more effectively inhibited.

Though unclear, the reason is considered to be due to several points including 1) when the solvent of the silica particle dispersion is removed, since the supercritical carbon dioxide has a property of "not exhibiting interfacial tension", the solvent may be removed without causing aggregation of the particles resulting from a liquid bridging force produced when the solvent is removed, 2) due to a property of supercritical carbon dioxide, which is "supercritical carbon dioxide is carbon dioxide under a temperature and a pressure that are equal to or higher than a critical point, and has both the diffusibility of gas and the solubility of liquid", the solvent is dissolved by being efficiently brought into contact with the supercritical carbon dioxide at a relatively low temperature (for example, 250° C. or lower), and accordingly, when the supercritical carbon dioxide in which the solvent is dissolved is removed, the solvent in the silica particle dispersion may be removed without generating coarse powder such as secondary aggregates caused by the condensation of silanol groups, and 3) if the surface of silica particles is subjected to hydrophobizing treatment using a hydrophobizing agent just like a metal compound, the hydrophobizing treatment is performed not only on the surface of the silica particles but also on the portion deep inside the cavities, and the like.

Herein, the solvent removing step, the surface treatment step, and the hydrophobizing treatment step may be performed separately. However, these steps are preferably performed consecutively (that is, the respective steps are preferably performed in a state not open to the atmospheric pressure). The respective steps are consecutively performed, and after the solvent removing step, the silica particles are prevented from adsorbing moisture so as to create a state where an excessive amount of moisture is inhibited from being adsorbed onto the silica particles. In this state, the surface treatment step and the hydrophobizing treatment step are performed. By doing this, there is no need to use a large amount of metal compound and hydrophobizing agent, or to excessively heat the particles to accelerate the reaction at a high temperature so as to perform the surface treatment step and the hydrophobizing treatment step. Consequently, silica composite particles having excellent environmental stability of the electrical resistance and chargeability are more effectively prepared, and the formation of coarse powder is more effectively inhibited.

Hereinafter, the method of preparing silica composite particles that uses supercritical carbon dioxide in other preparation processes will be described in detail in each of separate steps.

In addition, the method of preparing silica composite particles according to the exemplary embodiment is not limited to the above, and may include embodiments such as 1) an embodiment of using supercritical carbon dioxide only in the surface treatment step, 2) an embodiment of preparing dry silica particles in advance and performing the surface treatment step and the hydrophobizing treatment step sequentially on the particles, and 3) an embodiment of performing the respective steps separately.

Hereinafter, the respective steps will be described in detail.

Dispersion Preparing Step

In the dispersion preparing step, for example, a silica particle dispersion which contains silica particles and a solvent containing alcohol and water is prepared.

Specifically, in the dispersion preparing step, for example, a silica particle dispersion is manufactured and prepared by a wet method (for example, a sol-gel method). Particularly, the silica particle dispersion is preferably manufactured by a sol-gel method as a wet method, specifically, by generating silica particles by causing a reaction (a hydrolysis reaction and a condensation reaction) between a tetraalkoxysilane and a solvent containing alcohol and water, in the presence of an alkaline catalyst.

A volume average particle diameter of the silica particles is, for example, preferably from 10 nm to 500 nm and more preferably from 20 nm to 300 nm.

The volume average particle diameter of the silica particles is obtained as a 50% diameter (D50v) in a cumulative frequency of a volume particle size measured by LS Coulter (a particle size analyzer manufactured by Beckman Coulter, Inc.).

The shape of silica particles may be either spherical or irregular, but in view of fluidity or heat-resistance stability, the silica particles preferably have an irregular shape having a circularity of, for example, from 0.5 to 0.85.

The circularity of the silica particles is an average circularity of primary particles, and is obtained as "100/SF2" calculated from the following formula by analyzing an image of primary particles of the silica particles attached onto the surface of resin particles, by using image analysis software WinROOF (manufactured by MITANI CORPORATION).

$$\text{Circularity}(100/SF2) = 4\pi \times (A/I^2)$$

(In the formula, I represents a perimeter of particles in an image, and A represents a projected area of the particles.)

In addition, the average circularity is obtained as a 50% circularity in a cumulative frequency of the circularity of 100 primary particles obtained by the above image analysis.

In the dispersion preparing step, for example, when the silica particles are obtained by a wet method, the particles are obtained in a state of a dispersion in which silica particles are dispersed in a solvent (silica particle dispersion).

Herein, when the process moves on to the solvent removing step, a weight ratio of water to alcohol in the silica particle dispersion prepared is, for example, preferably from 0.1 to 1.0, more preferably from 0.15 to 0.5, and even more preferably from 0.2 to 0.3.

If the weight ratio of water to alcohol in the silica particle dispersion is set within the above range, coarse powder of the silica particles is generated less after the hydrophobizing treatment, and silica particles that are hydrophobized to a high degree and have excellent electrical resistance are easily obtained.

If the weight ratio of water to alcohol is less than 0.1, in the solvent removing step, silanol groups on the surface of the silica particles are condensed less when the solvent is removed. Accordingly, the amount of moisture adsorbed onto the surface of the silica particles having undergone the solvent removal increases, so the electrical resistance of the silica particles having undergone the hydrophobizing treatment is lowered too much in some cases. Moreover, if the weight ratio of water exceeds 1.0, in the solvent removing step, a large amount of water remains at a point in time when the removal of the solvent in the silica particle dispersion is almost completed. Therefore, the silica particles easily aggregate with each other due to a liquid bridging force and become coarse powder after the hydrophobizing treatment in some cases.

In addition, when the process moves on to the solvent removing step, a weight ratio of water to silica particles in the silica particle dispersion prepared is, for example, preferably from 0.02 to 3, more preferably from 0.05 to 1, and even more preferably from 0.1 to 0.5.

If the weight ratio of water to silica particles in the silica particle dispersion is set within the above range, coarse powder of silica particles is generated less, and silica particles that are hydrophobized to a high degree and have excellent electrical resistance are easily obtained.

If the weight ratio of water to silica particles is less than 0.02, in the solvent removing step, silanol groups on the surface of the silica particles are condensed to an extremely small extent when the solvent is removed. Accordingly, a large amount of moisture is adsorbed onto the surface of the silica particles having undergone the solvent removal, so the electrical resistance of the silica particles is lowered too much in some cases.

In addition, if the weight ratio of water exceeds 3, in the solvent removing step, a large amount of water remains at a point in time when the removal of the solvent in the silica particle dispersion is almost completed. Therefore, the silica particles easily aggregate with each other due to a liquid bridging force in some cases.

Further, when the process moves on to the solvent removing step, a weight ratio of silica particles to the silica particle dispersion prepared is, for example, preferably from 0.05 to 0.7, more preferably from 0.2 to 0.65, and even more preferably from 0.3 to 0.6.

If the weight ratio of the silica particles to the silica particle dispersion is less than 0.05, in the solvent removing step, the amount of supercritical carbon dioxide used becomes large, so productivity deteriorates in some cases.

If the weight ratio of the silica particles to the silica particle dispersion exceeds 0.7, a distance between silica particles is shortened in the silica particle dispersion, so coarse powder resulting from the aggregation or gelation of the silica particles is easily formed in some cases.

Solvent Removing Step

The solvent removing step is, for example, a step of removing the solvent of the silica particle dispersion by passing supercritical carbon dioxide.

That is, in the solvent removing step, supercritical carbon dioxide is added so as to be brought into contact with the silica particle dispersion, whereby the solvent is removed.

Specifically, in the solvent removing step, for example, the silica particle dispersion is put into a closed reaction container. Thereafter, liquefied carbon dioxide is put into the closed reaction container and heated, and the internal pressure of the reaction container is increased using a high-pressure pump to place the carbon dioxide in a supercritical state. Subsequently, the supercritical carbon dioxide is generated in the closed reaction container and discharged.

In this manner, while dissolving the solvent (alcohol and water), the supercritical carbon dioxide is also discharged to the outside the silica particle dispersion (outside the closed reaction container) at the same time together with the solvent entrained, whereby the solvent is removed.

Herein, the supercritical carbon dioxide is carbon dioxide under a temperature and pressure that are equal to or higher than a critical point and has both the diffusibility of gas and the solubility of liquid.

A temperature condition for the solvent removal, that is, the temperature of the supercritical carbon dioxide is, for example, preferably from 31° C. to 350° C., more preferably from 60° C. to 300° C., and even more preferably from 80° C. to 250° C.

If the temperature is lower than the above range, the solvent is not easily dissolved in the supercritical carbon dioxide, and this makes it difficult to remove the solvent. In addition, it is considered that coarse powder may be easily formed due to a liquid bridging force of the solvent or the supercritical carbon dioxide. On the other hand, if the temperature exceeds the above range, it is considered that coarse powder such as secondary aggregates may be easily formed due to the condensation of silanol groups on the surface of the silica particles.

A pressure condition for the solvent removal, that is, the pressure of the supercritical carbon dioxide is, for example, preferably from 7.38 MPa to 40 MPa, more preferably from 10 MPa to 35 MPa, and even more preferably from 15 MPa to 25 MPa.

If the pressure is lower than the above range, the solvent tends not to be easily dissolved in the supercritical carbon dioxide. On the other hand, if the pressure exceeds the above range, the cost of facilities tends to increase.

The amount of the supercritical carbon dioxide injected into and discharged from the closed reaction container is, for example, preferably from 15.4 L/min/m$^3$ to 1540 L/min/m$^3$, and more preferably from 77 L/min/m$^3$ to 770 L/min/m$^3$.

If the injected and discharged amount is less than 15.4 L/min/m$^3$, productivity tends to easily deteriorate since it takes a time for removing the solvent.

On the other hand, if the injected and discharged amount is 1540 L/min/m$^3$ or more, the time during which the supercritical carbon dioxide is in contact with the silica particle dispersion is shortened due to the short passage of the supercritical carbon dioxide. Accordingly, the solvent tends not to be easily removed efficiently.

Surface Treatment Step

The surface treatment step is, for example, a step of treating the surface of the silica particles with a metal compound in supercritical carbon dioxide, after the solvent removing step.

That is, in the surface treatment step, for example, while the reaction container is not open to the atmosphere before the process moves on from the solvent removing step, the surface of the silica particles is treated with a metal compound in the supercritical carbon dioxide.

Specifically, in the surface treatment step, for example, the supercritical carbon dioxide injected into and discharged from the closed reaction container in the solvent removing step is stopped being injected and discharged, and then the internal temperature and pressure of the closed reaction container are adjusted. In addition, in a state where the supercritical carbon dioxide is present in the closed reaction container, a metal compound is put into the container in a certain proportion based on the silica particles. In addition, while this state is being maintained, that is, in the supercritical carbon dioxide, the metal compound is reacted, thereby treating the surface of the silica particles.

Moreover, in the solvent removing step, if the metal compound is added before water and alcohol are removed, hydrolysis and a condensation reaction of the metal compound are not caused appropriately, aggregated particles are formed, or the metal compound is easily liberated and aggregated in some cases.

Herein, in the surface treatment step, notwithstanding that the metal compound needs to be reacted in the supercritical carbon dioxide (that is, under the atmosphere of the supercritical carbon dioxide), the surface treatment may be performed while the supercritical carbon dioxide is being passed (that is, while the supercritical carbon dioxide is being injected into and discharged from the closed reaction container), or may be performed without the passing of the supercritical carbon dioxide.

In the surface treatment step, the amount (that is, the charged amount) of the silica particles based on the volume of the reactor is, for example, preferably from 30 g/L to 600 g/L, more preferably from 50 g/L to 500 g/L, and even more preferably from 80 g/L to 400 g/L.

If the amount is smaller than the above range, a density of the metal compound based on the supercritical carbon dioxide decreases, and the probability of the contact between the metal compound and the surface of silica decreases, which makes it difficult for the reaction to proceed. On the other hand, if the amount is larger than the above range, a density of the metal compound based on the supercritical carbon dioxide increases, and the metal compound does not fully dissolve in the supercritical carbon dioxide and causes a dispersion defect, whereby coarse aggregates are easily formed.

A density of the supercritical carbon dioxide is, for example, preferably from 0.10 g/ml to 0.80 g/ml, more preferably from 0.10 g/ml to 0.60 g/ml, and even more preferably from 0.2 g/ml to 0.50 g/ml.

If the density is lower than the above range, solubility of the metal compound in the supercritical carbon dioxide decreases, whereby aggregates tend to be formed. On the other hand, if the density is higher than the above range, the diffusibility of the supercritical carbon dioxide into the pores of silica deteriorates, such that the surface treatment may be performed insufficiently. Particularly, for sol-gel silica particles containing a large amount of silanol groups, it is desirable to perform the surface treatment within the above density range.

The density of the supercritical carbon dioxide is adjusted by the temperature, pressure, and the like.

Herein, the metal compound is a metal compound in which a metal atom selected from a group consisting of Ti, Al, Zr, V, and Mg binds to an organic group via an oxygen atom.

In view of obtaining silica composite particles having excellent environmental stability of the electrical resistance and chargeability, the metal atom is preferably Ti or Al. That is, the metal compound is preferably a metal compound in which a metal atom selected from a group consisting of Ti and Al binds to an organic group via an oxygen atom.

Specific examples of the metal compound include metal compounds such as alkoxides (for example, a methoxide, an ethoxide, an n-propoxide, an i-propoxide, an n-butoxide, an i-butoxide, a sec-butoxide, and a tert-butoxide), and chelates or acylates (for example, β-diketones such as acetyl acetonate; β-ketoesters such as ethyl acetoacetate; amines such as triethanolamine; and carboxylic acids such as acetic acid, butyric acid, lactic acid, and citric acid).

Here, in view of promoting the formation of a Si—O-M bond between a metal atom M and a Si atom, and in view of the controllability of the reaction rate and the shape, particle size, and particle size distribution of the silica composite particles obtained, the metal compound is preferably a metal compound having one or more (preferably two or more) alkoxy groups. That is, the metal compound is preferably a metal compound in which one or more (preferably two or more) alkoxy groups (alkyl groups binding to a metal atom via oxygen) bind to a metal atom.

In addition, the number of carbon atoms of the alkoxy group is preferably 8 or less and more preferably from 1 to 4, in view of the controllability of the reaction rate and the shape, particle size, and particle size distribution of the silica particles obtained.

Among the metal compounds, examples of titanium compounds include tetra-i-propoxy titanium, tetra-n-butoxy titanium, tetra-t-butoxy titanium, di-i-propoxy-bis(ethylacetoacetate)titanium, di-i-propoxy-bis(acetylacetonate) titanium, di-i-propoxy-bis(triethanolaminate)titanium, di-i-propoxytitanium-diacetate, and di-i-propoxytitanium-dipropionate.

Examples of aluminum compounds include triethoxy aluminum, tri-i-propoxy aluminum, tri-sec-butoxy aluminum, di-i-propoxy-mono-sec-butoxy aluminum, and di-i-propoxy aluminum-ethyl acetoacetate.

Examples of zirconium compounds include tetra-n-propoxy zirconium, tetra-i-propoxy zirconium, and tetra-n-butoxy zirconium.

Examples of vanadium compounds include vanadium oxytriethoxide, vanadium oxytri-n-propoxide, vanadium oxytri-i-propoxide, vanadium oxytri-n-butoxide, vanadium oxytri-i-butoxide, and vanadium oxytri-sec-butoxide.

Examples of magnesium compounds include magnesium ethoxide.

The amount of the metal compound used (added) is preferably from 0.01% by weight to 10% by weight, more preferably from 0.1% by weight to 5% by weight, and even more preferably from 0.2% by weight to 3% by weight based on the silica particles, in terms of a weight obtained by converting the metal atoms in the metal compound into metal oxides (for example, $TiO_2$ for a titanium compound, $AlO_{3/2}$ for an aluminum compound, $ZrO_2$ for a zirconium compound, $VO_{5/2}$ for a vanadium compound, and MgO for a magnesium compound).

If the amount of the metal compound used is smaller than the above range, it is difficult to improve the environmental stability of the electrical resistance and chargeability in some cases. If the amount of the metal compound used exceeds the above range, the electrical resistance decreases, or aggregates are formed by the liberation of the unreacted metal compound or the condensation reaction of the metal compound in some cases.

In addition, the metal compound may be used alone, or may be used as a solution that is a mixture of the metal compound and a solvent easily dissolving the metal compound. Examples of the solvent include toluene, methyl ethyl ketone (MEK), and the like.

Herein, a temperature condition of the surface treatment (temperature condition during the reaction), that is, the temperature of the supercritical carbon dioxide is, for example, preferably from 80° C. to 300° C., more preferably from 100° C. to 250° C., and even more preferably from 120° C. to 200° C.

If the temperature is lower than the above range, the reactivity between the metal compound and the surface of the silica particles deteriorates in some cases. On the other hand, if the temperature exceeds the above range, the condensation reaction is caused between the silanol groups of the silica particles, so the particles are aggregated in some cases. Particularly, for sol-gel silica particles containing a large amount of silanol groups, it is desirable to perform the surface treatment within the above temperature range.

Meanwhile, a pressure condition (pressure condition during the reaction) of the hydrophobizing treatment, that is, the pressure of the supercritical carbon dioxide is, for example, preferably from 8 MPa to 30 MPa, more preferably from 10 MPa to 25 MPa, and even more preferably from 15 MPa to 20 MPa, even though the pressure simply needs to be under such a condition that satisfies the above density.

Hydrophobizing Treatment Step

The hydrophobizing treatment step is a step of treating the surface of the silica particles with a hydrophobizing agent in the supercritical carbon dioxide, after the surface treatment step.

That is, in the hydrophobizing treatment step, for example, while the reaction container is not open to the atmosphere before the process moves on from the surface treatment step, hydrophobizing treatment is performed on the surface of the silica particles by using a hydrophobizing agent in the supercritical carbon dioxide.

Specifically, in the hydrophobizing treatment step, for example, while the internal temperature and pressure of the closed reaction container in the surface treatment step are being maintained, or, after the internal temperature and pressure of the closed reaction container are adjusted to be suitable for the hydrophobizing treatment, a hydrophobizing agent is put into the closed reaction container in a certain ratio based on the silica particles, in a state where the supercritical carbon dioxide is present. Thereafter, while this state is being maintained, that is, in the supercritical carbon dioxide, the hydrophobizing agent is reacted to perform the hydrophobizing treatment on the silica particles. In addition, after the reaction ends, the pressure of the closed reaction container is reduced, and the container is cooled.

Herein, in the hydrophobizing treatment step, notwithstanding that the hydrophobizing treatment needs to be performed in the supercritical carbon dioxide (that is, under the atmosphere of the supercritical carbon dioxide), the hydrophobizing treatment may be performed while the supercritical carbon dioxide is being passed (that is, while the supercritical carbon dioxide is being put into and discharged from the closed reaction container), or may be performed without the passing of the supercritical carbon dioxide.

In the hydrophobizing treatment step, the amount (that is, the charged amount) of the silica particles based on the volume of the reactor is, for example, preferably from 30 g/L to 600 g/L, more preferably from 50 g/L to 500 g/L, and even more preferably from 80 g/L to 400 g/L.

If the amount is smaller than the above range, a density of the hydrophobizing agent based on the supercritical carbon dioxide decreases, and the probability that the agent may contact the surface of silica is lowered, whereby the hydrophobizing reaction does not easily proceed in some cases. On the other hand, if the amount is larger than the above range, a density of the hydrophobizing agent based on the supercritical carbon dioxide increases, and the hydrophobizing agent does not fully dissolve in the supercritical carbon dioxide and causes a dispersion defect, whereby coarse aggregates are easily formed.

A density of the supercritical carbon dioxide is, for example, preferably from 0.10 g/ml to 0.80 g/ml, more preferably from 0.10 g/ml to 0.60 g/ml, and even more preferably from 0.2 g/ml to 0.50 g/ml.

If the density is lower than the above range, solubility of the hydrophobizing agent in the supercritical carbon dioxide is lowered, so aggregates tend to be formed. On the other hand, if the density is higher than the above range, diffusibility of the supercritical carbon dioxide into the pores of silica deteriorates, and accordingly, the hydrophobizing treatment may be performed insufficiently in some cases. Particularly, for sol-gel silica particles containing a large amount of silanol groups, it is desirable to perform the hydrophobizing treatment within the above range of density.

In addition, the density of the supercritical carbon dioxide is adjusted by the temperature, pressure, and the like.

Examples of the hydrophobizing agent include known silicon compounds having an alkyl group (for example, a methyl group, an ethyl group, a propyl group, and a butyl group). Specific examples thereof include silazane compounds (for example, silane compounds such as methyltrimethoxysilane, dimethyldimethoxysilane, trimethylchlorosilane, and trimethylmethoxysilane, hexamethyldisilazane, and tetramethyldisilazane), and the like. One kind of the hydrophobizing agent may be used, or plural kinds thereof may be used.

Among these hydrophobizing agents, silicon compounds having a trimethyl group, such as trimethylmethoxysilane and hexamethyldisilazane, are suitable.

The amount of the hydrophobizing agent used is not particularly limited. However, in order to obtain the effects of hydrophobizing, the amount is, for example, preferably from 0.1% by weight to 60% by weight, more preferably from 0.5% by weight to 40% by weight, and even more preferably from 1% by weight to 30% by weight, based on the silica particles.

Herein, a temperature condition of the hydrophobizing treatment (temperature condition during the reaction), that is, the temperature of the supercritical carbon dioxide is, for example, preferably from 80° C. to 300° C., more preferably from 100° C. to 250° C., and even more preferably from 120° C. to 200° C.

If the temperature is lower than the above range, the reactivity between the hydrophobizing agent and the surface of the silica particles deteriorates in some cases. On the other hand, if the temperature exceeds the above range, a condensation reaction is caused between silanol groups of the silica particles, whereby aggregates are formed in some cases. Particularly, for sol-gel silica containing a large amount of silanol groups, it is desirable to perform the hydrophobizing treatment within the above temperature range.

Meanwhile, a pressure condition of the hydrophobizing treatment (pressure condition during the reaction), that is, the pressure of the supercritical carbon dioxide is, for example, preferably from 8 MPa to 30 MPa, more preferably from 10

MPa to 25 MPa, and even more preferably from 15 MPa to 20 MPa, even though the pressure simply needs to be under such a condition that satisfies the above density.

Through the respective steps described so far, the silica composite particles are obtained.

EXAMPLES

Hereinafter, the exemplary embodiment will be described in more detail based on examples and comparative examples, but the exemplary embodiment is not limited to those examples. In addition "part(s)" indicates "part(s) by weight" unless otherwise specified.

Example A

Example A1

In the manner shown below, the surface treatment using a metal compound and the hydrophobizing treatment using a hydrophobizing agent are performed on the silica particles. In addition, for the surface treatment and hydrophobizing treatment, an instrument including a carbon dioxide cylinder, a carbon dioxide pump, an entrainer pump, a stirrer-attached autoclave (volume of 500 ml) and a pressure valve is used.

First, 20 parts of powder of hydrophilic fumed silica particles having a volume average particle diameter of 12 nm is put into the stirrer-attached autoclave (volume of 500 ml).

Thereafter, liquefied carbon dioxide is injected into the autoclave and the pressure is increased by the carbon dioxide pump while the temperature is being increased by a heater, thereby generating a supercritical state of 150° C. and 15 MPa inside the autoclave. After the stirrer is rotated at 100 rpm, 2 parts (0.56 part in terms of $TiO_2$) of tetra-i-propoxy titanium is added into the autoclave by the entrainer pump, and the resultant is held as is for 30 minutes under stirring. Subsequently, 3 parts of hexamethyldisilazane is further added into the autoclave by using the entrainer pump, and the resultant is held as is for 30 minutes under stirring. Thereafter, stirring is stopped, and the pressure valve is opened such that the internal pressure of the autoclave becomes the atmospheric pressure, and the temperature is decreased to room temperature (25° C.)

In this manner, the surface treatment using a metal compound and the hydrophobizing treatment using a hydrophobizing agent are performed sequentially, thereby obtaining silica composite particles.

Example A2

Silica composite particles are obtained in the same manner as in Example A1, except that 2 parts of tetra-i-propoxy titanium is changed to 4 parts (0.94 part in terms of $TiO_2$) of tetra-n-butoxy titanium.

Example A3

Silica composite particles are obtained in the same manner as in Example A1, except that 2 parts of tetra-i-propoxy titanium is changed to 2 parts (0.37 part in terms of $AlO_{2/3}$) of di-i-propoxy aluminum-ethyl acetoacetate.

Example B

Example B1

Preparation of Silica Particle Dispersion A 205 parts of methanol and 33 parts of 10% aqueous ammonia are added into a 1.5 L glass reaction container including a stirrer, a dripping nozzle, and a thermometer, followed by mixing, thereby obtaining an alkaline catalyst solution. After the temperature of the alkaline catalyst solution is adjusted to 30° C., while the mixture is being stirred, a flow rate is adjusted such that the amount of $NH_3$ per 1 mol of tetraalkoxysilane that is the total amount of tetraalkoxysilane supplied per minute becomes 0.27 mol, and 100 parts of tetramethoxysilane and 79 parts of 3.8% aqueous ammonia are started to be added thereto simultaneously. Thereafter, the components are added dropwise for 60 minutes, thereby obtaining a dispersion (solid content concentration of 9.5% by weight) of hydrophilic silica particles with an irregular shape that have a volume average particle diameter of 120 nm and a circularity of 0.82. In addition, the amount of the tetraalkoxysilane supplied is set to 0.0018 mol/(mol·min) based on a mole number of alcohol in the alkaline catalyst solution.

Thereafter, the obtained silica particle dispersion is concentrated to yield a solid content concentration of 40% by weight by using a rotary filter R-fine (manufactured by KOTOBUKI INDUSTRIES CO., LTD.). The concentrated resultant is named a silica particle dispersion A.

Preparation of Silica Composite Particles

In the following manner, the solvent removing step is performed on the silica particle dispersion, and the surface treatment using a metal compound and the hydrophobizing treatment using a hydrophobizing agent are performed on the silica particles. In addition, for the surface treatment and the hydrophobizing treatment, an instrument including a carbon dioxide cylinder, a carbon dioxide pump, an entrainer pump, a stirrer-attached autoclave (volume of 500 ml), and a pressure valve is used.

First, 300 parts of the silica particle dispersion A is put into the stirrer-attached autoclave (volume of 500 ml), and the stirrer is rotated at 100 rpm. Thereafter, liquefied carbon dioxide is injected into the autoclave, and the pressure is increased by the carbon dioxide pump while the temperature is being increased by a heater, thereby creating a supercritical state of 150° C. and 15 MPa inside the autoclave. While the internal pressure of the autoclave is being kept at 15 MPa by the pressure valve, supercritical carbon dioxide is passed by the carbon dioxide pump, thereby removing methanol and water from the silica particle dispersion A.

Subsequently, at a point in time when the amount (cumulative amount: measured as an amount of passed carbon dioxide in a standard state) of the passed supercritical carbon dioxide reaches 100 parts, the passing of the supercritical carbon dioxide is stopped.

Thereafter, in a state where the temperature is kept at 150° C. by the heater, the pressure is kept at 15 MPa by the carbon dioxide pump, and the supercritical state of carbon dioxide in the autoclave is maintained, 4 parts (1.12 g in terms of $TiO_2$) of tetra-i-propoxy titanium is added into the autoclave by the entrainer pump, and the resultant is held as is for 30 minutes under stirring. Then 24 parts of hexamethyldisilazane is further added into the autoclave by the entrainer pump, and the resultant is held as is for 30 minutes under stirring. Subsequently, stirring is stopped, and the pressure valve is opened such that the internal pressure of the autoclave becomes the atmospheric pressure, and the temperature is decreased to room temperature (25° C.).

In this manner, the solvent removing step, the surface treatment using a metal compound, and the hydrophobizing treatment using a hydrophobizing agent are performed sequentially, thereby obtaining silica composite particles.

Example B2

Silica composite particles are obtained in the same manner as in Example B1, except that 4 parts of tetra-i-propoxy titanium is changed to 3.2 parts (0.59 part in terms of $AlO_{2/3}$) of di-i-propoxy aluminum-ethyl acetoacetate.

Example B3

Silica composite particles are obtained in the same manner as in Example B1, except that 4 parts of tetra-i-propoxy titanium is changed to 8 parts (1.76 parts in terms of $TiO_2$) of di-i-propoxy-bis(acetylacetonate) titanium.

Example B4

Silica composite particles are obtained in the same manner as in Example B1, except that 4 parts of tetra-i-propoxy titanium is changed to a tetra-i-propoxy zirconium solution obtained by dissolving 2 parts (0.75 part in terms of $ZrO_2$) of tetra-i-propoxy zirconium in 5 parts of toluene.

Example B5

Silica composite particles are obtained in the same manner as in Example B1, except that 4 parts of tetra-i-propoxy titanium is changed to 2 parts (0.75 part in terms of $VO_{5/2}$) of vanadium oxy tri-i-propoxide.

Example B6

Silica composite particles are obtained in the same manner as in Example B1, except that 4 parts of tetra-i-propoxy titanium is changed to 2 parts (0.58 part in terms of MgO) of magnesium ethoxide.

Example B7

Silica composite particles are obtained in the same manner as in Example B1, except that 24 parts of hexamethyldisilazane in Example B1 is not added.

Comparative Examples

Comparative Example 1

Silica composite particles are obtained in the same manner as in Example A1, except that the surface treatment using a metal compound in Example A1 is performed open to the atmosphere.

Comparative Example 2

Silica composite particles are obtained in the same manner as in Example B1, except that after 300 parts of the silica particle dispersion A is put into the stirrer-attached autoclave (volume of 500 ml), 4 parts (1.12 g in terms of $TiO_2$) of tetra-i-propoxy titanium is put while the stirrer is being rotated at 100 rpm so as to perform the surface treatment using a metal compound open to the atmosphere, and then liquefied carbon dioxide is injected into the autoclave and supercritical carbon dioxide is passed by the carbon dioxide pump while the internal pressure of the autoclave is being kept at 15 MPa so as to remove methanol and water.

Evaluation

The characteristics of the silica composite particles obtained in the respective examples are evaluated. The respective characteristics are as follows. The results are shown in Table 1.

Environmental Dependency of Electrical Resistance

The environmental dependency of electrical resistance is evaluated as follows.

On the surface of a circular jig on which an electrode plate of 20 $cm^2$ is disposed, the silica composite particles to be measured are loaded at a thickness of from 1 mm to 3 mm, thereby forming a silica composite particle layer. On this layer, the same electrode plate of 20 $cm^2$ as above is disposed such that the silica composite particle layer is interposed between the electrode plates. In order to remove gaps between the silica composite particles, a load of 4 kg is applied onto the electrode plate disposed on the silica composite particle layer, and then the thickness (cm) of the silica composite particle layer is measured. An electrometer and a high-voltage power generator are connected to both the electrodes on the top and bottom of the silica composite particle layer. A high voltage is applied such that the electric field between both electrodes reaches a predetermined value, and a current value (A) flowing at this time is read, thereby calculating a volume resistivity ($\Omega \cdot cm$) of the silica composite particles. A formula for calculating the volume resistivity ($\Omega \cdot cm$) of the silica composite particles is as follows:

$$\rho = E \times 20 / \{(I-I_0) \times L\}.$$

In addition, in the formula, $\rho$ represents a volume resistivity ($\Omega \cdot cm$) of the silica composite particles, E represents an applied voltage (V), I represents a current value (A), $I_0$ represents a current value (A) at the time when the applied voltage is 0 V, and L represents a thickness (cm) of the silica composite particle layer respectively. A log value of the calculated volume resistivity ($\Omega \cdot cm$) is taken as a "value of volume resistivity", and in the present evaluation, a volume resistivity at the time when the applied voltage is 1000 V is used. Moreover, the measurement is performed in a high-temperature and high-humidity environment (28° C., 85% RH) and a low-temperature and low-humidity environment (10° C., 15% RH) respectively. From the ratio between the values obtained from each environment, the environmental dependency of the volume resistivity is evaluated.

Environmental dependency of volume resistivity=(value of volume resistivity of high-temperature and high-humidity environment)÷(value of volume resistivity of low-temperature and low-humidity environment)

The evaluation criteria are as follows.

A: An environmental dependency of a value of volume resistivity is 0.8 or more.
B: An environmental dependency of a value of volume resistivity is 0.7 or more and less than 0.8.
C: An environmental dependency of a value of volume resistivity is 0.6 or more and less than 0.7.
D: An environmental dependency of a value of volume resistivity is 0.5 or more and less than 0.6.
E: An environmental dependency of a value of volume resistivity is less than 0.5.

Environmental Dependency of Chargeability

The environmental dependency of chargeability is evaluated as follows.

3 parts of silica composite particles are mixed with 100 parts of spherical styrene/butyl acrylate (85/15) copolymer resin particles (weight average molecular weight Mw=60,000) having a volume average particle diameter of 8 μm, for 60 seconds by a sample mill, thereby preparing silica composite particle-attached resin particles. 3 parts of the silica composite particle-attached resin particles are mixed with 30 parts of ferrite carrier having a volume average particle diameter of 50 μm for 120 seconds by a Turbula mixer, and then left in a high-temperature and high-humidity environment (28°

C., 85% RH) and a low-temperature and low-humidity environment (10° C., 15% RH) respectively overnight, and a blow-off charge amount is measured.

Environmental dependency of chargeability=(charge amount of high-temperature and high-humidity environment)÷(charge amount of low-temperature and low-humidity environment)

The evaluation criteria are as follows.

A: An environmental dependency of chargeability is 0.8 or more.
B: An environmental dependency of chargeability is 0.7 or more and less than 0.8.
C: An environmental dependency of chargeability is 0.6 or more and less than 0.7.
D: An environmental dependency of chargeability is 0.5 or more and less than 0.6.
E: An environmental dependency of chargeability is less than 0.5.

Proportion of Coarse Powder

A proportion of coarse powder is measured by LS Coulter and obtained as a proportion of particles of 1 μm or larger.

The evaluation criteria are as follows.

A: A proportion of coarse particles of 1 μm or larger is 1% by volume or less.
B: A proportion of coarse particles of 1 μm or larger is 5% by volume or less and more than 1% by volume.
C: A proportion of coarse particles of 1 μm or larger is 10% by volume or less and more than 5% by volume.
D: A proportion of coarse particles of 1 μm or larger is 20% by volume or less and more than 10% by volume.
E: A proportion of coarse particles of 1 μm or larger exceeds 20% by volume.

TABLE 1

|  | Environmental dependency of electrical resistance | Environmental dependency of chargeability | Proportion of coarse powder |
|---|---|---|---|
| Example A1 | B | B | A |
| Example A2 | B | A | B |
| Example A3 | B | B | A |
| Example B1 | B | B | A |
| Example B2 | A | A | A |
| Example B3 | A | A | A |
| Example B4 | B | C | B |
| Example B5 | B | C | B |
| Example B6 | C | C | B |
| Example B7 | C | B | A |
| Comparative Example 1 | D | E | D |
| Comparative Example 2 | E | E | E |

From the above results, it is understood that the present examples yield superior results in all of the evaluations of the environmental dependency of electrical resistance, environmental dependency of chargeability, and the proportion of coarse powder, compared to comparative examples.

The foregoing description of the exemplary embodiments of the present invention has been provided for the purposes of illustration and description. It is not intended to be exhaustive or to limit the invention to the precise forms disclosed. Obviously, many modifications and variations will be apparent to practitioners skilled in the art. The embodiments were chosen and described in order to best explain the principles of the invention and its practical applications, thereby enabling others skilled in the art to understand the invention for various embodiments and with the various modifications as are suited to the particular use contemplated. It is intended that the scope of the invention be defined by the following claims and their equivalents.

What is claimed is:

1. A method of preparing silica composite particles, comprising:
   treating silica particles,
   wherein the treating is for treating the silica particles with a metal compound in which a metal atom binds to an organic group via an oxygen atom, in supercritical carbon dioxide, and
   the metal atom is selected from a group consisting of Ti, Al, Zr, V, and Mg.

2. The method of preparing silica composite particles according to claim 1,
   wherein the metal atom is Ti or Al.

3. The method of preparing silica composite particles according to claim 1, further comprising:
   treating the surface of the silica particles of which the surface has been treated with the metal compound, with a hydrophobizing agent.

4. The method of preparing silica composite particles according to claim 1,
   wherein the silica particles are prepared by a sol-gel method.

5. The method of preparing silica composite particles according to claim 1,
   wherein an amount of the metal compound added is from 0.01% by weight to 10% by weight based on the silica particles.

6. The method of preparing silica composite particles according to claim 1,
   wherein in the treating, the temperature of the supercritical carbon dioxide is from 80° C. to 300° C.

7. The method of preparing silica composite particles according to claim 1,
   wherein a volume average particle diameter of the silica particles is from 10 nm to 500 nm.

8. The method of preparing silica composite particles according to claim 1,
   wherein a circularity of the silica particles is from 0.5 to 0.85.

9. The method of preparing silica composite particles according to claim 1,
   wherein a density of the supercritical carbon dioxide is in a range of from 0.10 g/ml to 0.80 g/ml.

10. A method of preparing silica composite particles, comprising:
    preparing a silica particle dispersion that contains silica particles and a solvent containing alcohol and water;
    removing the solvent from the silica particle dispersion by injecting supercritical carbon dioxide;
    treating the surface of the silica particles having undergone the solvent removal, in the supercritical carbon dioxide by using a metal compound in which a metal atom selected from a group consisting of Ti, Al, Zr, V, and Mg binds to an organic group via an oxygen atom; and
    treating the surface of the silica particles treated with the metal compound, in the supercritical carbon dioxide with a hydrophobizing agent.

11. The method of preparing silica composite particles according to claim 10,
    wherein the metal atom is Ti or Al.

12. The method of preparing silica composite particles according to claim 10,
    wherein the silica particles are prepared by a sol-gel method.

13. The method of preparing silica composite particles according to claim 10,
 wherein an amount of the metal compound added is from 0.01% by weight to 10% by weight based on the silica particles.

14. The method of preparing silica composite particles according to claim 10,
 wherein in the treating, a temperature of the supercritical carbon dioxide is from 80° C. to 300° C.

15. The method of preparing silica composite particles according to claim 10,
 wherein a volume average particle diameter of the silica particles is from 10 nm to 500 nm.

16. The method of preparing silica composite particles according to claim 10,
 wherein a circularity of the silica particles is from 0.5 to 0.85.

\* \* \* \* \*